United States Patent [19]

Bechgaard et al.

[11] Patent Number: 4,606,909

[45] Date of Patent: Aug. 19, 1986

[54] PHARMACEUTICAL MULTIPLE-UNITS FORMULATION

[75] Inventors: Helle Bechgaard, Hellerup; Peter Houmøller, Taastrup, both of Denmark

[73] Assignee: A/S Alfred Benzon, Copenhagen, Denmark

[21] Appl. No.: 622,393

[22] Filed: Jun. 20, 1984

Related U.S. Application Data

[63] Continuation of Ser. No. 524,465, Aug. 18, 1983, abandoned, which is a continuation of Ser. No. 328,538, Dec. 8, 1981, abandoned.

[30] Foreign Application Priority Data

Nov. 20, 1981 [DK] Denmark ............................ 5164/81

[51] Int. Cl.[4] .......................... A61K 9/22; A61K 9/24; A61K 9/28
[52] U.S. Cl. ........................................ 424/21; 424/19; 424/32; 424/33; 424/35
[58] Field of Search ..................................... 424/19-22, 424/32, 33, 35

[56] References Cited

U.S. PATENT DOCUMENTS

| | | | |
|---|---|---|---|
| 3,775,537 | 11/1973 | Lehmann et al. | 424/21 |
| 4,083,949 | 4/1978 | Benedikt | 424/19 |
| 4,173,626 | 11/1979 | Dempski et al. | 424/19 |
| 4,193,985 | 3/1980 | Bechgaard et al. | 424/35 |
| 4,291,016 | 9/1981 | Nougaret | 424/35 |

FOREIGN PATENT DOCUMENTS 0013262 12/1979 European Pat. Off. .
1468172 3/1973 United Kingdom .

OTHER PUBLICATIONS

Yamanouchi, C.A., 94, #127362r (1981).
Hazler, C.A., 91, #181467e (1979).
Martin, C.A., 93, #245473e (1980).
Elgindy, C.A., 96:11599k (1982).
Lindberg, C.A., 77, #66167f (1972).
Porebski, C.A., 75, #25335z (1971).
Borzunov, C.A., 75, #121361a (1971).
Biosrame, C.A., 97, #44255u (1982).
Toyo, C.A., 97, #44326t (1982).
Bogentoft, C.A., 96, #57792n (1982).
Dreher, C.A., 94, #109115h (1981).
Biosrame, C.A., 91, #181383z (1979).
Lehmann, C.A., 91, #9441f (1979).
El-Sayed, C.A., 89, #204156v (1978).
Lehmann, C.A., 84, #95546d (1976).
Lehmann, C.A., 81, #111411b, #68497v, #964404f (1974).
Dittgen, C.A., 85, #198123p (1976).
Kach, C.A., 86, #60497c (1977).
Dittgen, C.A., 87, #11555g, (1977).
Dittgen C.A. 87 #189376n (1977).
Baggensen, S. et al (1981) Pharm. Acta Helv., 56, 85–92.
Bechgaard et al (1978) Drug Develop. Ind. Pharm. 4, 53–67.
Bechgaard et al (1978) J. Pharm. Pharmacol., 30, 690–692.
Bechgaard et al (1980) J. Pharma. Sci., 69, 1327–1330.
Bogentoft, et al (1978) Eur. J. Clin. Pharmacol., 14, 351–355.
Green, DM (1966) J. New Drugs, 6, 294–303.
McDonald et al (1977) J. Clin. Pharmacol., 17, 601–606.
Snedecor et al (1967) Iowa State University Press, Iowa, 271–275.

*Primary Examiner*—Shep K. Rose
*Attorney, Agent, or Firm*—Stiefel, Gross, Kurland & Pavane

[57] ABSTRACT

A pharmaceutical oral controlled release multiple-units formulation in which individual units comprise cross-sectionally substantially homogeneous cores containing particles of a sparingly soluble active substance, the cores being coated with a coating which is substantially resistant to gastric conditions, but which is erodable under the conditions prevailing in the small intestine, in particular an enteric coating which is substantially insoluble at a pH below 7 such as Eudragit ® S (an anionic polymerizate of methacrylic acid and methacrylic acid methyl ester), is prepared by a process comprising comminuting an active substance together with a substance which is readily soluble in intestinal fluids such as an anionic detergent to obtain particles containing the active substance in intimate admixture with the readily soluble substance, combining the resulting particles into cross-sectionally substantially homogeneous cores together with components which accelerate the disintegration of the cores and intestinal fluids such as talc and saccharose, coating the individual cores with an erodable coating, and combining a multiplicity of the coated cores into a capsule or tablet formulation.

Such a coating may also be used when the active substance is a substance which exerts an irritating effect on the gastric mucosa and/or is unstable in an acidic environment.

18 Claims, 2 Drawing Figures

PHARMACEUTICAL MULTIPLE-UNITS FORMULATION

This is a continuation of application Ser. No. 524,465, filed Aug. 18, 1983, which is a continuation of application Ser. No. 328,538, filed Dec. 8, 1981, both now abandoned.

The present invention relates to oral pharmaceutical controlled release multiple-units dosage forms with important new features.

TECHNICAL BACKGROUND

Many physiological factors influence both the gastrointestinal transit time and the release of a drug from a controlled release dosage form and thus the uptake of the drug into the systemic circulation. Dosage forms should therefore be designed so that such variable factors do not compromise the efficacy and safety of the product.

In man, a reproducible gastrointestinal transit time of a depot formulation can be achieved only by a controlled release multiple-units dosage form.

The term "controlled release multiple-units formulation" (Bechgaard & Hegermann Nielsen, 1978) indicates a pharmaceutical formulation comprising a multiplicity (typically at least 100) of individual coated (or "microencapsulated") units contained in the formulation in such a form that the individual units will be made available from the formulation upon disintegration of the formulation in the stomach of the animal, including man, who has ingested the formulation. Typically, the multiple-units formulation may be a capsule which is disintegrated in the stomach to make available a multiplicity of individual coated units contained in the capsule, or a tablet which is disintegrated in the stomach to make available a multiplicity of coated units originally combined in the tablet.

Drug release from a controlled release dosage form is generally controlled either by diffusion through a coating or by erosion of a coating by a process dependent on, e.g., enzymes or pH. The importance of a pH independent diffusion with respect to obtaining a reproducible rate of availability and to minimizing intra- and intersubject variations is known (GB Pat. No. 1 468 172 and Bechgaard & Baggesen, 1980). It is also known that controlled drug release in vivo can be achieved through an erodable process by enteric coating of a multiple-units dosage form (Green, 1966; McDonald et al., 1977; Bogentoft et al., 1978).

Both above-mentioned types of controlled release multiple-units formulation techniques aim at a controlled release of active substance at a predetermined pattern to reduce and delay the peak plasma level without affecting the extent of drug availability. Due to a lower peak plasma level, the frequency of undesired side-effects may be reduced, and due to the delay in the time to obtain peak plasma level and the extension of the time at the therapeutically active plasma level, the dosage frequency may be reduced to once or twice daily dosage in order to improve patient compliance.

A further advantage of the controlled release multiple-units dosage form is that high local concentrations of the active substance in the gastrointestinal system is avoided, due to the units being distributed freely throughout the gastrointestinal tract, independent of gastric emptying. If the mucosa of the stomach is more sensitive to the active substance than the intestinal mucosa, controlled release formulations avoiding release of active substance in the gastric area will be preferred; formulations of this type are controlled release multiple-units formulations in which the coatings are substantially resistant to gastric conditions.

DISCLOSURE OF INVENTION

The present invention relates to new developments in controlled release multiple-units formulations where the individual units are coated with an erodable coating.

According to the invention, active substances are incorporated in pharmaceutical oral controlled release multiple-units formulations in which individual units comprise cross-sectionally substantially homogeneous cores containing particles of an active substance, the cores being coated with a coating which is substantially resistant to gastric conditions but is erodable under the conditions prevailing in the small intestine.

The individual units of the multiple-units formulations according to the invention will normally be pellets (coated cores) in which the core is constituted by a combination of active substance and excipients. A type of core which is widely used in the known art (vide, e.g., Eur. Patent Application No. 79 850 110) is a substantially spherical particle of a size of about 0.5-1 mm consisting of excipient(s) with active substance applied to its surface. Typical cores of this type are the so-called "non-pareil" cores where the excipients are in the form of spherical particles of saccharose. It is also known, e.g., from GB Patent Specification No. 1 468 172, to prepare cores which are cross-sectionally substantially homogeneous, but these known cross-sectionally substantially homogeneous cores were coated with a diffusion coating. It is believed that it has not previously been suggested to combine cores which are cross-sectionally substantially homogeneous with an erodable coating. In the present context, the term "cores which are cross-sectionally substantially homogeneous" designates cores in which the active substance is not confined to an exterior layer on the core body, in other words normally cores which, through the cross-section of the core body, contain substantially the same type of composition comprising microparticles containing active substance, in contrast to the non-pareil type of cores which each consist of an excipient body with active substance applied to its surface, and in contrast to coated crystal units which are substantially monolithic crystals. From this definition, it will be understood that the cores which are cross-sectionally substantially homogeneous will normally consist of a mixture of active substance with excipient(s), (and in spite of the term "homogeneous", this mixture will not necessarily be qualitatively or quantitatively homogeneous through the cross-section of the particle but may show, e.g., a concentration gradient of one or more of its constituents) or they may consist substantially solely of active substance in a non-monolithic form, e.g. as a sintered mass of crystalline or amorphous particles of active substance. In the following specification and claims, such cores which are cross-sectionally substantially homogeneous will, for brevity, often simply be designated "cores".

The erodable coatings used in the formulations of the present invention are coatings which are substantially resistant under gastric conditions but are eroded during the passage of the unit through the small intestine. Erodable coatings may be coatings which are eroded by process dependent upon, e.g., enzymes present in the segment of the intestine where the erosion is desired, including enzymes generated by the animal, including man, to whom the unit is administered and enzymes produced by bacteria, or bacterial fermentation of the erodable coating. As has been explained above, erodable coatings are distinguished from diffusion coatings which are substantially insoluble and non-erodable in gastrointestinal fluids, but are permeable, by diffusion, to gastrointestinal fluids and dissolved active substance. (For the sake of completeness, however, it should be noted that although the quantitatively predominant contribution to the absorption from erodably coated units is the phase after the coating has been eroded, it cannot be precluded that a certain amount of active substance will be released through the uneroded coating by diffusion).

An important class of erodable coatings for use in the formulations according to the present invention are the so-called enteric coatings which are coatings that are substantially insoluble under the pH conditions prevailing in the stomach but are soluble at a pH prevailing in the small intestine, typically a pH of above 4.5.

DETAILED DESCRIPTION OF INVENTION

Cores

According to the invention, the cores are cross-sectionally substantially homogeneous cores. The combination of cross-sectionally substantially homogeneous cores with a coating which is substantially resistant to gastric conditions but is erodable under the conditions prevailing in the small intestine offers several advantages compared to the known art erodably coated cores.

Firstly, cross-sectionally substantially homogeneous cores are easy to produce in large scale in reproducible manner in, e.g., automatic equipment because the components therefor are normally simply mixed in the prescribed proportions, which means that the inter-core variation in composition, e.g., concentration of active substance, can be kept within narrow limits. Secondly, the concentration of active substance in the core can be varied within very wide limits (generally between 10-90% by weight), which renders it possible to optimize the concentration of active substance in the single core in order to minimize capsule sizes for a given dosage strength and thereby optimize patience compliance. Thirdly, the size of the cores may be easily adjusted as desired, to improve the distribution pattern of the units throughout the gastrointestinal tract; this is in contrast to the non-pareil technique where the size variation is limited by the available standard sizes. Fourthly, the composition of the cores may be optimized with respect to the extent of drug availability, i.e., to enhance the release of the active substance in the small intestine, after erosion of the coating.

Thus, it is possible to utilize special measures to enhance the absorption of the active substances by enhancing the disintegration of the cores and the dissolution of the active substance. One such special measure according to the invention is to provide the active substance in the cores in the form of particles of a size of about 1-10 μm, in particular about 2-5 μm, in admixture with components enhancing the disintegration of the cores and the dispersion of the active substance in intestinal fluids.

The cores are typically made by granulating these particles together with excipients, including bulk agents such as carbohydrates and derivatives thereof such as starch and starch derivatives, including microcrystalline cellulose, binders such as cellulose derivatives, including methylcellulose or hydroxypropylmethylcellulose, polyethylene glycol, polyvinylpyrrolidone, agar, or gelatin, such as by treatment in a high speed mixer (to directly obtain compact-shaped cores), or by treatment in a planet mixer with subsequent extrudation of the mixture into strings of predermined diameter close to the desired final cross-sectional dimension of the cores and treatment of the strings in a marumerizer or similar equipment to obtain compact-shaped cores. The diameter of the cores is normally adapted so that the coated core has a diameter of about 0.4-1.2 mm, in particular about 0.5-1.0 mm, especially about 0.5-0.8 mm, such as 0.5-0.7 mm. The preferred diameter of the coated cores is about 0.5-0.6 mm. By incorporating special ingredients in the mixture, an increased tendency to disintegrate in contact with intestinal fluids may be imparted to the cores. Examples of such materials are solid insoluble materials which will tend to counteract excessive compaction of the content of the cores during their preparation, and/or to introduce slidability between the components in the cores, and/or to geometrically introduce tensions in the cores, and/or to interfere with the packing of the content of the cores to provide voids between the particles containing active substance, such as plate-shaped bodies, e.g., talc, or compact-shaped particles of a particle size of about 20-100 μm, in particular about 50-75 μm, such as aluminium silicate, zinc oxide, magnesium oxide, titanium dioxide, colloidal silica, or magnesium trisilicate.

According to a particular aspect of the invention, the disintegration of the cores is additionally enhanced when particles of a substance which is readily soluble in intestinal fluids are incorporated in the mixture from which the cores are made. Examples of such substances are saccharose, glucose, mannitol, sorbitol, or lactose.

In particular, it is preferred to enhance the disintegration of the cores in intestinal fluids by a combination of the two above-mentioned measures that is, by incorporation of both insoluble and a soluble disintegration-enhancing component. One example of a combination of this kind is the combination of talc and saccharose which is illustrated in the examples.

The possibility of enhancing the disintegration of the cores is especially valuable in connection with active substances which are sparingly soluble and which, therefore, should be exposed to the intestinal fluids as effectively and fast as possible after erosion of the coating. In order to obtain maximum disintegration, it is preferred to use only a small amount of binder, if any, in the mixture from which the cores are made.

The weight ratio between the active substance(s) and the excipients may vary within wide limits. As a general rule, the cores may contain 10-90% by weight of active substance. When the active substance is a sparingly soluble substance, the amount of disintegration-enhancing components (insoluble and/or soluble) will often be at least 20% by weight, typically at least 40% by weight, calculated on the total mixture.

In accordance with a particular aspect of the invention, the predetermined controlled release of the active substance may be changed by changing the density of the cores, and thus, the time of appearance of the cores in the predetermined segment of the intestine may be varied at will. By increasing the density of the cores with resulting increased transit time of the coated cores (Bechgaard & Ladefoged, 1978), a more delayed and longer lasting absorption phase is obtained, that is a longer period during which the absorption of the active substance takes place after the substance has been released, and thereby made available for absorption, by erosion of the coating.

Examples of excipients which may be used to increase the density of the cores are described in U.S. Pat. No. 4,193,985 and include heavy particulate substances such as barium sulphate, titanium oxide, zinc oxides, and iron salts.

Active Substance

The active substance in the formulations according to the invention may be any active substance which is advantageously administered in a controlled release multiple-units formulation to be made available in the small intestine, in particular drug substances, including, e.g., methyldopa, morphine, naproxene, prazosin, theophyllin, verapamil, amilorid, and disopyramide.

Especially important formulations according to the invention are formulations in which the active substance, apart from being a substance about which it is known or indicated from a pharmacokinetic and/or clinical point of view that it is advantageously administered in a controlled release multiple-units formulation, is a substance which exerts an irritating effect on the gastric mucosa such as acetylsalicylic acid, indomethacin, and other non-steroid antiinflammatory drugs, and/or is unstable in acidic environment such as erythromycin, iron salts, cardiac glycosides, e.g., digoxin, and L-Dopa, and/or is sparingly soluble.

The pharmaceutical formulation according to the invention is of particular importance in connection with sparingly soluble active substances, as these are difficult to formulate in accordance with known controlled release dosage forms based on the diffusion principle.

In the present context, the term "sparingly soluble substance" designates a substance which requires more than 30 parts by volume of water to dissolve 1 part by weight of the active substance at ambient temperature. Examples of sparingly soluble active substances are found among almost all therapeutic groups, including diuretics, antiepileptics, sedatives, antiarrhythmics, antirheumatics, $\beta$-blockers, vasodilators, analgesics, bronchodilators, hormones, oral antidiabetics, antihypertensives, anti-inflammatories, and antidepressives.

Among the sparingly soluble substances, important substances belong to a group which requires more than 1000 parts by volume of water to dissolve 1 part by weight of the active substance at ambient temperature, or even more than 10,000 parts by volume of water.

As examples of sparingly soluble active substances which may be formulated according to this aspect of the invention may be mentioned indomethacin, spironolactone, ibuprofen, furosemide, sulfadiazine, sulfamerazine, progesterone, reserpine, pyrvinium embonate, mofebutazone, hydrochlorothiazide, tetracycline, tolbutamide, acetaminophen, testosterone, valproic acid, estradiol, acetazolamide, erythromycin, iron salts, hydralazine, carbamazepine, quinidine, and cardiac glycosides, e.g., digoxin.

As examples of substances among the above-mentioned sparingly soluble substances which require more than 1000 parts by volume of water to dissolve 1 part by weight of the substance at ambient temperature may be mentioned spironolactone, ibuprofen, furosemide, hydrochlorothiazide, tolbutamide, and testosterone.

By utilization of the principle of the invention, it is possible to obtain an extent of availability of a sparingly soluble active substance which is equal to or better than the extent of availability of plain formulations and to reduce and delay the peak plasma level compared to plain formulations. This is achieved by utilizing (i) the fact that the units are freely distributed throughout the gastrointestinal tract, independent of gastric emptying, as the units are small enough to pass the pylorus even when the sphincter is closed, and (ii) the fact that there is a significant physiological variation along the gastrointestinal tract, including variation in pH and qualitative and quantitative composition of enzymes and microflora. In the stomach, the pH range is wide, viz. pH 1–6, primarily due to increase in pH after intake of food, while the pH in the small intestine ranges from 5 to 8. The variation in the physiological environment along the small intestine may be utilized by adapting the erodable coating to be eroded in a desired segment of the small intestine. The above-mentioned measures to enhance the disintegration of the cores are preferably used in combination with special techniques for enhancing the dissolution of the active substance which are explained below in connection with the discussion of the particles containing active substance.

Particles Containing Active Substance

The active substance is normally present in the cores in the form of particles of a size in the range of from about 1 to about 75 $\mu$m. Normally, the particles are of the conventional sizes in which the particular active substances are available. While active substances which are readily soluble may be available in any size within the range stated above, sparingly soluble substances are typically available as ground materials having particle sizes in the range of about 1–10 $\mu$m, and this range, in particular the range of about 2–5 $\mu$m, is normally suitable for sparingly soluble active substances for incorporation in the cores of the present invention.

According to a particularly important embodiment of the invention, active substances which are sparingly soluble are incorporated in the cores in the form of particles in which they are in intimate admixture with a substance which is readily dissolved in intestinal fluids and which, therefore, enhances the dispersion of the active substance. Such an intimate admixture may be obtained, e.g., by co-comminuting the active substance together with the dispersion-enhancing substance, both substances preferably being in solid form during the comminution. The co-comminution may be performed by subjecting a mixture of particles of the active substance with particles of the dispersion-enhancing substance to grinding, in particular high shear grinding, e.g. in a pinned disc mill or a jet mill or other equipment exerting similar stress. The resulting intimate mixture will be in the form of particles in the range of 1–10 $\mu$m, in particular 2–5 $\mu$m, in which the active substance and the dispersion-enhancing substance are intimately combined with each other by conglomeration and/or adsorption. The particles in which a sparingly soluble active substance is combined with a dispersion-enhancing substance show enhanced dissolution of the active substance, which is believed to be due to the fact that the dispersion-enhancing substance incorporated in the particles enhances the dispersion of the active substance which is thereby more efficiently exposed to the intestinal fluids.

The dispersion-enhancing substance which is incorporated in the particles containing active substance may, in principle, by any pharmaceutically acceptable excipient which is readily soluble in intestinal fluids. Examples of such substances are saccharose, glucose, mannitol, sorbitol or lactose. Especially effective dispersion-enhancing substances are surface-active substances such as detergents, in particular anionic or nonionic detergents, for instance sodium salts of fatty alcohol sulphates, preferably sodium laurylsulphate, sulfosuccinates, partial fatty acid esters of sorbitans such as sorbitanmonooleate (SPAN ®), partial fatty acid esters of polyhydroxyethylene sorbitans such as polyethylene glycolsorbitan monooleate (Tween ® 80), or polyhydroxyethylene fatty alcohol ether such as polyhydroxyethylene (23) lauryl ether (BRIJ ® 35).

The amount of dispersion-enhancing substance which is incorporated in the particles containing active substance is normally less than 100%, calculated on the active substance, typically at the most 70%, calculated on the active substance. Thus, for instance, when the readily soluble substance is saccharose or another dispersion-enhancing carbohydrate, it is normally co-comminuted with the active substance in an amount of about 40–60% by weight, calculated on the active substance. When the dispersion-enhancing substance is a surface-active substance such as a detergent, it is preferably co-comminuted with the active substance in an amount of at the most 10% by weight, calculated on the active substance, preferably about 5% by weight.

Coating

The erodable coating applied to the cores according to the invention is preferably an enteric coating which is applied from a solution and/or suspension in an organic solvent and/or water. The application of the coating is typically performed in a fluidized bed or by pan coating.

Examples of enteric coating materials which may be used for the purpose of the present invention are coatings selected from the group consisting of acrylic polymers and copolymers, e.g. a polymerisate of methacrylic acid and methacrylic acid methyl ester such as Eudragit ® S 12,5, Eudragit ® S 12,5 P (which corresponds to Eudragit ® S 12,5 but contains 1.25% of dibutylphthalate), Eudragit ® 30 D or Eudragit ® L 12,5, shellac, cellulose acetate esters such as mixed partial esters of cellulose-containing phthalate groups, acetyl groups and free acid groups (cellulose acetate phthalate), polyvinyl acetate esters such as polyvinyl acetate phthalate, hydroxypropylmethyl cellulose esters such as hydroxypropylmethylcellulose phthalate, or alkyleneglycolether esters of copolymers such as partial ethyleneglycol monomethylether ester of ethylacrylate-maleic anhydride copolymer, propyleneglycol monomethylether ester of ethylacrylate-maleic anhydride copolymer, dipropyleneglycol monomethylether ester of ethylacrylate-maleic anhydride copolymer or diethyleneglycol monomethylether ester of methylacrylate-maleic anhydride copolymer, N-butylacrylate-maleic anhydride copolymer, isobutylacrylate-maleic anhydride copolymer or ethylacrylate-maleic anhydride copolymer.

The coating material may be admixed with various excipients such as plasticizers, inert fillers, e.g. talc, pigments, in a manner known per se.

The type and amount of enteric coating applied is adapted so as to obtain resistance to gastric environments and release in the desired segment of the small intestine. Normally, the amount of the coating will be about 2–25% by weight, calculated as dry coating weight on the total weight of the cores, typically about 4–12% by weight.

In accordance with one aspect of the present invention, the coating is selected so that it will be preferentially eroded in the distal part of the small intestine. An example of such a coating is an enteric coating which is substantially insoluble at pH below 7.

In the present context, the term "an enteric coating which is substantially insoluble at pH below 7" designates an enteric coating which, under the experimental conditions defined under MATERIALS AND METHODS below, releases less than 15% of the active substance contained in the coated core within one hour at pH 6.5.

Preferably, the coating which is substantially insoluble at pH below 7 will, at the same time, effectively release a high proportion of the active substance, typically more than 90% of the active substance contained in the core, within one hour at pH 7.5.

Preferred materials for enteric coatings which are substantially insoluble at pH below 7 are polymerisates of methacrylic acid and methacrylic acid methyl ester or mixtures thereof. A specific example of such a coating material is Eudragit ® S.

The use of a coating which is selectively or preferentially eroded in the distal part of the small intestine offers several advantages:

Firstly, due to the longer travel of the units through the small intestine to reach the distal section of the small intestine in which the pH is in the range of 7–8, the time to reach peak plasma concentration is increased.

It is known that physiological pH variations in the distal segment of the small intestine are small. Furthermore, pH variations caused by food intake are also low in the distal segment. Due to these very stable pH conditions, controlled release formulations of the invention in which the coating is one that is substantially insoluble at pH below 7 will yield a highly reproducible absorption phase, both within and between subjects and are therefore preferred.

As appears from Example 5, the standard deviations of the bioavailability parameters of a formulation according to the invention where the coating was an enteric coating which is substantially insoluble at pH below 7 were of the same order of magnitude when the formulation was administered with food or after a fast, respectively. The administration of the coated cores concomittant to food intake did not influence the extent of availability.

The aspect of the invention comprising controlled release multiple-units formulations in which the coating is an erodable coating which is selectively eroded in the distal part of the small intestine, in particular an enteric coating which is substantially insoluble at pH below 7, is of general importance and advantage in connection with any type of units, including units which are not cross-sectionally substantially homogeneous.

Therefore, one aspect of the present invention relates to a pharmaceutical oral controlled release multiple-units formulation in which individual units comprising an active substance are coated with a coating which is selectively eroded in the distal part of the small intestine. The coating is preferably an enteric coating which is substantially insoluble at a pH below 7, and especially a coating which will release at least 90% of the active substance within one hour at a pH of 7.5 under the experimental conditions defined under MATERIALS AND METHODS below.

Hence, according to this aspect of the invention, the units may be any type of units used in multiple-units formulations. Interesting units, apart from the cross-sectionally substantially homogeneous cores discussed above, are units of the non-pareil type (including such units with a concentration gradient of the active substance along the radius of the core), and crystals. The active substances which are formulated according to this aspect of the invention are typically the same as mentioned above. The preparation of the units according to this aspect of the invention is performed by coating the desired unit types in the same manner as described above.

Figure 1:
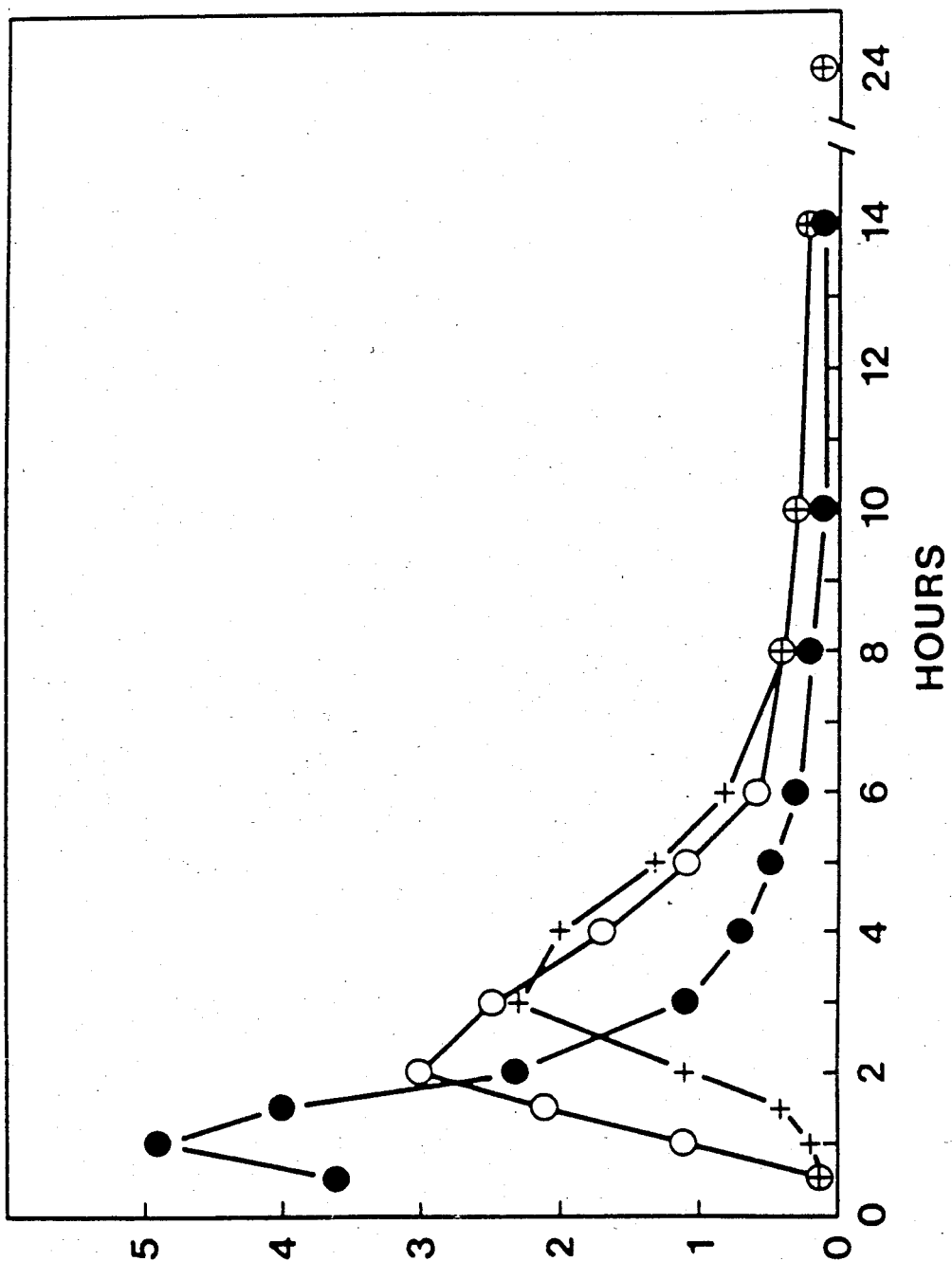
FIG. 1 is a graph showing the mean concentrations of indomethacin in plasma after single oral doses of 75 mg in the form of a reference formulation (indicated by filled-in circles) or in the form of Coating A capsules according to the invention (indicated by circles) or Coating B capsules according to the invention (indicated by crosses). The concentrations are the ones stated in Example 4.

The invention is illustrated in greater detail in the following experimental section.

MATERIALS AND METHODS

In the examples, the following materials were used:
Indomethacin:
  (2-[1-(4-Chlorobenzoyl)-5-methoxy-2-methylindol-3-yl]acetic acid); BP 80.
Sodium laurylsulphate:
  Ph Eur
Microcrystalline cellulose:
  BPC 79.
Saccharose powder:
  Ph Eur
Talc:
  Ph Eur
Purified water:
  Ph Eur
Eudragit ® S 12,5:
  An anionic polymerisate of methacrylic acid and methacrylic acid methyl ester having a dry matter content of 12.5%, a density $D^{20}$ of 0.84, a viscosity at 20° C. of 100 cP; supplied by Röhm Pharma GmbH, Darmstadt, Germany.
Eudragit ® L 12,5:
  An anionic polymerisate of methacrylic acid and methacrylic acid methyl ester having a dry matter content of 12.5%, a density of $D^{20}$ of 0.84, and a viscosity at 20° C. of 75 cP; supplied by Röhm Pharma GmbH, Darmstadt, Germany.
Eudragit ® L 30 D:
  An anionic polymerisate of methacrylic acid and methacrylic acid methyl ester having a dry matter content of 30% as an aqueous dispersion, supplied by Röhm Pharma GmbH, Darmstadt, Germany.
Acetyltributylcitrate:
  Citroflex ® A-4; supplied by Pfizer A/S, Copenhagen, Denmark.
Isopropanol:
  BP 80.
Polyvinylpyrrolidone:
  BP 80 Add 81.
Furosemide:
  (4-Chloro-N-furfuryl-5-sulfamoylantranilic acid) BP 80.
Acetylsalicylic acid:
  Ph Eur
Triacetin:
  (1,2,3-propanetrioltriacetate) USP XX.

Determination of in vitro dissolution of pellets or cores:
  In vitro dissolution rates were determined according to Baggesen et al (1981). The rotation speed was 30±1 r.p.m. and the dissolution medium was 250 ml of 0.1M hydrochloric acid (pH 1.2) or citrate buffer (0.05M, pH 4.5 or 0.02M, pH 6.5) or phosphate buffer (0.05M, pH 7.5), maintained at 37±0.1° C. Release of active substance into the dissolution medium was determined by measuring the absorbance spectrophotometrically at 320 nm (indomethacin), 271 nm (furosemide) or 278 nm (the isobestic point of acetylsalicylic acid/salicylic acid).

Example 1

Preparation of Indomethacin-Containing Cores to be Coated with an Enteric Coating Cores (containing 24% talc) were prepared from 2.9 kg indomethacin, 0.2 kg sodium laurylsulphate, 0.5 kg microcrystalline cellulose, 4.0 kg saccharose powder and 2.4 kg talc.

The indomethacin and the sodium laurylsulphate were co-comminuted by passage through a grinder using a 0.5 mm sieve.

The ground mixture was mixed with the microcrystalline cellulose, the saccharose and the talc in a planet mixer.

10 kg of the resulting mixture were moistened with 0.8 kg purified water and were mixed in a planet mixer until the mixture was a little lumpy.

The moist mixture was extruded through a 0.5 mm sieve. The first kgs of extrudate passing the sieve were powdery and were reextruded. The resulting extrudate were strings breaking off in lengths of 10–30 cm.

2 kg of the extruded strings were formed into compact-shaped cores in a marumerizer, and the resulting compact-shaped cores were dried in a fluidized bed dryer and sieved through a separator, the upper sieve being 0.71 mm, and the bottom sieve 0.46 mm.

In a similar manner as described above, cores (containing 10% talc) were prepared from 2.9 kg indomethacin, 0.2 kg sodium laurylsulphate, 1.0 kg microcrystalline cellulose, 4.9 kg saccharose powder, and 1.0 kg talc.

The release of the indomethacin was measured, at pH 7.5, as described under MATERIALS AND METHODS, for the cores containing 24% talc and 10% talc, respectively. The amount of indomethacin released at pH 7.5 after 10 minutes appears from Table I.

Table I

| Percentage of indomethacin released at pH = 7.5 after 10 min (n = 2) | |
|---|---|
| Cores with 24% talc | 98.4% |

Table I-continued

| Percentage of indomethacin released at pH = 7.5 after 10 min (n = 2) | |
| --- | --- |
| Cores with 10% talc | 60.0% |

It appears from Table I that the increase of the talc content from 10% to 24% results in an increase of the release of indomethacin to practically quantitative release within 10 minutes.

Coating of Cores with Enteric Coating

An enteric coating suspension was prepared by homogenizing 9.0 kg Eudragit® S 12,5 together with 0.135 kg acetyltributylcitrate, 0.9 kg talc and 7.965 kg isopropanol.

10 kg of the above-described cores containing 24% talc were coated with 4.167 kg of this coating suspension in a fluidized bed, and the resulting pellets were covered with talcum.

For the preparation of a pharmaceutical dosage form, more than 1000 of these pellets were filled in a capsule No. 1. Each capsule contained 75 mg indomethacin.

Example 2

The Effect of Dispersion-Enhancing Agents with Respect to Improving the Dissolution of the Active Substance In a similar manner as described in Example 1, (but without cocomminution of the indomethacin with any dispersion-enhancing agent), cores were prepared from 3.2 kg indomethacin, 1.0 kg microcrystalline cellulose, 5.7 kg saccharose powder and 0.1 kg polyvinylpyrrolidone. These cores are designated cores, type 0.

Another portion of cores, designated cores, type SACH, was prepared from the same ingredients in a similar manner, except that in this case the indomethacin and the saccharose powder were co-comminuted by passage through a grinder using a 0.5 mm sieve.

In the same manner as described in Example 1, cores were made from 3.2 kg indomethacin, 0.2 kg sodium laurylsulphate, 1.0 kg microcrystalline cellulose, 5.5 kg saccharose powder and 0.1 kg polyvinylpyrrolidone. These cores are designated cores, type NaLS.

The release of the indomethacin was measured, at pH 7.5, as described under MATERIALS AND METHODS for these 3 types of cores.

The amount of indomethacin released at pH 7.5 after 10 minutes appears from Table II.

Table II

| Percentage of indomethacin released at pH = 7.5 after 10 min (n = 2) | |
| --- | --- |
| Cores, Type 0 | 71.0% |
| Cores, Type SACH | 92.8% |
| Cores, type NaLS | 97.1% |

It appears from Table II that the release of indomethacin is considerably increased when a dispersion-enhancing agent is co-comminuted with the indomethacin, and that the detergent type of dispersion-enhancing agent results in the fastest release.

EXAMPLE 3

The Influence of Coatings Soluble at Different pH on the Dissolution of Indomethacin An enteric coating suspension was prepared as described in Example 1 from 2.08 kg Eudragit® L12.5, 2.08 kg Eudragit® S12.5, 0.0625 kg acetyltributylcitrate, 0.417 kg talc and 3.69 kg isopropanol.

This coating, which is soluble at pH above 6.5, was called Coating A.

An enteric coating suspension was prepared as described in Example 1 from 4.16 kg Eudragit® S12.5, 0.0625 kg acetyltributylcitrate, 0.417 kg talc and 3.69 kg isopropanol.

This coating, which is soluble at pH above 7.0, was called Coating B. Cores containing sodium laurylsulphate and 24% talc, prepared as described in Example 1, were coated with 10% Coating A or 10% Coating B (% dry matter of coating, calculated on the weight of the core). The dissolution of indomethacin from the resulting two types of pellets was determined as described under MATERIALS AND METHODS. The results are stated in Table III.

Table III

| Percentage of indomethacin released at pH 6.5 and pH 7.5 (n = 3) | | | | |
| --- | --- | --- | --- | --- |
| | pH = 6.5 | | | pH = 7.5 |
| | 10 m | 30 m | 60 m | 60 m |
| Coating A | 17.4 | 64.0 | 76.5 | 98.6 |
| Coating B | 6.5 | 9.0 | 9.8 | 100.7 |

It appears from Table III that cores coated with Coating A and Coating B quantitatively released the indomethacin at pH 7.5 within 60 minutes and that cores coated with Coating B only released about 10% indomethacin after 1 h at pH 6.5. The possibility of adjusting the enteric coating is very important because it makes it possible to tailor-make formulations to be disintegrated in a predetermined segment of the small intestine.

Example 4

Bioavailability of Indomethacin from two Multiple-units Controlled Release Formulations Drug formulations:

The two types of indomethacin-containing pellets prepared in Example 3 (designated Coating A and Coating B, respectively) were formulated into hard gelatin capsules designated Coating A and Coating B capsules, respectively. Each capsule of each formulation contained 75 mg indomethacin. Instant release capsules of indomethacin (Indocid®, Merck, Sharp and Dohme Ltd.) were used as the reference formulation. Each capsule of the reference formulation contained 25 mg indomethacin. Indomethacin was almost completely released from this capsule formulation during 10 minutes at pH 6.5.

Drug administration:

Eight healthy normal adult male subjects of age range 21–24 years and bodyweight range 60–80 kg were selected for this study.

Each subject fasted for 12 hours before drug administration and remained fasting for 4 hours afterwards. Administration was conducted in a three-way crossover with one week between dosing, in which each subject received orally one Coating A or B capsule or three capsules of the reference formulation (75 mg total dose) together with 100 ml water. Blood samples (10 ml) were withdrawn before dosing and at intervals during 24 hours afterwards.

Measurement of indomethacin in plasma:

Concentrations of indomethacin in plasma were measured using a high performance liquid chromatographic (HPLC) method. Plasma (200 μl for concentrations between 0.1 μg/ml and 4 μg/ml or 100 μl for concentrations above 4 μg/ml containing 1 μg mefenamic acid as an internal standard) was mixed with phosphate buffer (1 ml, 1M pH 5.0), and extracted with freshly distilled diethyl ether (5 ml) for 10 minutes on a rotary mixer. The phases were separated by centrifugation and the organic phase was removed and evaporated to dryness under nitrogen at 37° C. The residue was washed to the bottom of the tube with a small amount of ether which was then evaporated to dryness.

The drug residues were dissolved in methanol (50 μl), portions (20 μl) of which were injected into the HPLC system which consisted of an automatic injector and pump (Waters Associates Ltd., U.K.), fitted with a variable wavelength ultra-violet monitor (Pye Unicam Ltd., U.K.) operated at 260 nm (λmax for indomethacin in methanol). The stainless steel column (30 cm × 0.4 cm i.d.) was prepacked with μ Bondapak $C_{18}$ (mean particle size 10 μm, Waters Associates Ltd.) and a stainless steel precolumn (7 cm × 0.2 cm i.d.) drypacked with pellicular Co:Pell® ODS (particular size 25–37 μm, Whatman Ltd., UK) was installed to protect the analytical column. Chromatography was performed in reversed-phase mode with a mobile phase of acetonitrile (62%, v/v) in phosphate buffer (0.1M, pH 4.0) at a flow rate of 2.5 ml/min. Indomethacin and the internal standard (mefenamic acid) were eluted with retention times of 2.7 and 3.6 minutes respectively.

Linear calibration curves of peak area ratio of indomethacin to internal standard were constructed by analysis of plasma containing these compounds over the concentration range 0.1 μg/l–4 μg/l. The standard error of taking the calibration line as a measure of indomethacin concentration over this range was 0.12 μg/ml. The recovery of the internal standard at the level added of 5 μg/ml was 100% ± 4 S.D. (n = 5), and the mean recovery of indomethacin over the concentration range 0.5 μg/l–4 μg/l was 103% ± 3 S.D. (n = 5). No peaks were present on chromatograms of extracts of predose plasma in the position of the internal standard, but in some samples of predose plasma, interfering material was present at the position of indomethacin and equivalent to a maximum of 0.1 μg/ml. The limit of detection was therefore arbitrarily set at 0.1 μg/ml. The precision of measurement was assessed by the coefficients of variation of the means of replicate measurements (n = 6) of ±17% at 0.1 μg/ml, ±2% at 2 μg/ml and ±4% at 4 μg/ml. Known metabolites of indomethacin did not interfere with the measurement of the unchanged drug above a limit of 0.1 μg/ml.

Data processing:

Areas to 24 h (AUC) under the plasma concentration-time curves were calculated by the trapezoidal rule. Since plasma drug levels at 24 h after dosing were close to the limit of detection, these areas were considered to be equivalent to infinite time. Since drug administration was unbalanced with respect to the dosing sessions, AUCs, peak plasma levels and their times of occurrence, times to reach a plasma level of 1.0 μg/ml were subjected to analysis of variance by regression techniques. Overall formulation-related effects were examined by the F-test and formulation means were tested pair-wise by the method of least significant differences (Snedecor & Cochran, 1967).

Results:

Peaks of mean plasma concentrations of indomethacin of 4.9 μg/ml, 3.0 μg/ml and 2.3 μg/ml occurred after single oral doses of 75 mg of the reference formulation and the Coating A and B capsule formulations respectively and these peaks of mean levels occurred at 1 h, 2 h and 3 h respectively, vide FIG. 1.

Indomethacin was more slowly absorbed from both Coating A and B capsules than from the reference capsules, and was more slowly absorbed from the Coating B capsules than it was from the Coating A capsules.

The bioavailability parameters appear in Table IV. The differences between formulations within these parameters are highly significant except for the AUC.

TABLE IV

Mean values of bioavailability parameters of indomethacin after administration of the reference and coating A and B capsules, respectively. Standard deviations are in parentheses

|  | Reference | Coating A | Coating B |
|---|---|---|---|
| Area (μg h/ml) | 12.2 (4.0) | 13.7 (4.3) | 11.8 (2.4) |
| Peak plasma level (μg/ml) | 5.5 (1.2) | 3.8 (1.2) | 2.9 (0.8) |
| Time of peak level (h) | 1.0 (0.3) | 2.1 (0.6) | 3.5 (0.9) |
| Time to 1 μg/ml$^a$ (h) | 0.4 (0.2) | 1.2 (0.3) | 2.4 (0.7) |

$^a$Time after dosing required to reach a plasma level of 1 μg/ml, by interpolation.

These data imply a considerable slower absorption rate after administration of the Coating B capsules compared with Coating A and the reference formulations. The extent of bioavailability, however, was similar after administration of each preparation.

Discussion:

Formulation of indomethacin as multiple-units controlled-release capsules comprising enteric-coated pellets of different sensitivity to an alkaline environment did not affect the extent of drug bioavailability, and drug absorption was slower after administration of these pellets when compared with the standard reference formulation. Rates of absorption were in the order: reference formulation > Coating A capsules > Coating B capsules (Table IV); thus it was demonstrated that these absorption rates are ranked in order of their observed dissolution rates in vitro (Table III). The present formulation technique takes into account the transit time and distribution of the pellets throughout the gastrointestinal tract (Bechgaard & Ladefoged, 1978) and the characteristic of a strictly alkaline-dependent erosion of the coating of pellets. The data confirm that the drug release from these pellets in vivo was dependent on an alkaline pH and that dissolution probably occurred in the distal part of the gastrointestinal tract, where the pH is relatively high (pH 6.5–7.5) and less variable than that in the proximal small intestine, which factor is more important in the non-fasting state. This finding is further supported by the low observed standard deviations of the bioavailability parameters after administration of the Coating A and B capsules (Table IV). These standard deviations were of the same order of magnitude as those after administration of the standard reference formulation. Thus the present multiple-units controlled release formulations represent a reliable and reproducible source of indomethacin.

Example 5

The Effect of Food on the Bioavailability of Indomethacin from a Multiple-units Controlled Release Formulation Drug formulation:

Coating B capsules each containing 75 mg indomethacin, as described in Example 4.

Drug administration:

Nine healthy adult male subjects, age range 22-36 years and bodyweight ranges 63-70 kg, were selected for this study.

Administration was conducted as a complete crossover with one week between doses, in which each subject received a single oral dose of one capsule (75 mg) together with 100 ml water, once after a 12 hours fast, and once after the subject had received a breakfast consisting of cereal, egg, bacon and sausage, one slice of toast and one cup of coffee, within 15 minutes of drug administration. Blood samples were withdrawn before dosing, and at intervals during 24 hours afterwards.

Measurement of indomethacin in plasma:

Concentrations of indomethacin in plasma were measured by a high performance liquid chromatographic method, as described in Example 4.

Data processing:

Areas to 24 h (AUC) under the plasma concentration-time curves were calculated by the trapezoidal rule. Peak plasma levels and times of their occurence, AUC, and times to reach a plasma level of 1 $\mu$g/ml were subjected to analyses of variance for crossover designs (Snedecor & Cochran, 1967), with subjects, dosing sessions, treatments and residual as factors in the analysis. The statistical significance of treatment differences was tested by the method of least significant differences.

Figure 2:
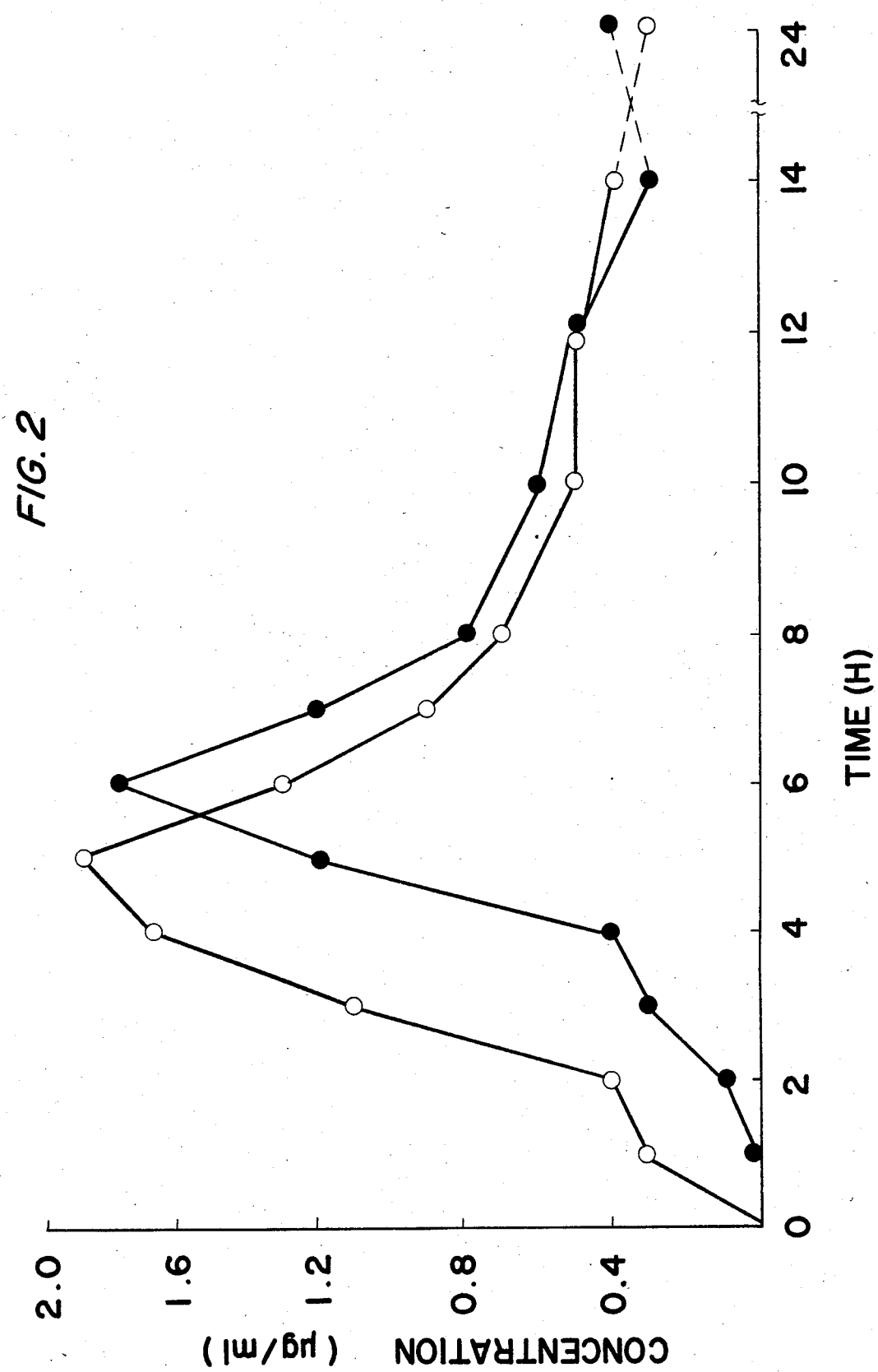
FIG. 2 illustrates the mean plasma concentration of indomethacin after single oral doses of 75 mg as Coating B capsules according to the invention after 12 h fast (indicated by circles) or within 15 min of ingestion of food (indicated by filled-in circles). The concentrations are the ones stated in Example 5.

Results:

A peak of mean concentrations of indomethacin in plasma of 1.9 $\mu$g/ml occurred at 5 hours after administration of 75 mg after a 12 h fast, and indomethacin was present (0.2 $\mu$g/ml) in plasma withdrawn 24 h after dosing. When 75 mg was administered within 15 min of ingestion of a substantial breakfast, the peak of mean plasma levels of indomethacin (1.8 $\mu$g/ml) occurred at 6 h and thereafter mean plasma indomethacin concentrations declined to 0.4 $\mu$g/ml at 24 hours, vide FIG. 2.

Two peak levels of indomethacin concentrations were present in plasma of most subjects after administration with fasting and also with food, but this effect was more noticeable when the doses were administered with food. Indomethacin is thought to undergo enterohepatic recirculation in man, and the secondary peak plasma levels may have been an expression of this recirculation.

The overall major peak plasma concentrations and AUC were not significantly different ($P > 0.05$) after administration of Coating B capsules either after a 12 h fast or with food (Table V)

Table V

| Mean bioavailability parameters of indomethacin. Standard deviations in parentheses (n = 9) | | | | | |
|---|---|---|---|---|---|
| | Fasting | | With food | | |
| Area ($\mu$g.h/ml) | 13.8 | (3.8) | 12.5 | (2.6) | NS |
| Peak level (ng/ml): | | | | | |
| First | 2.7 | (0.8) | 2.2 | (1.0) | NS |
| Second | 0.5[a] | (0.2) | 1.1[b] | (0.8) | NS |
| Time of peak level (h): | | | | | |
| First | 4.2 | (1.4) | 6.4 | (2.2) | $P < 0.05$ |
| Second | 12.7 | (1.0) | 14.4 | (6.8) | NS |
| Time (h) to reach 1 $\mu$g/ml[a] | 3.0 | (1.3) | 5.5 | (2.6) | $P < 0.05$ |

[a]Secondary peak levels were present in the plasma of 6 subjects
[b]Secondary peak levels were present in the plasma of 7 subjects
Significance levels refer to treatment differences from the analysis of variance. NS = not significant ($P > 0.05$)

The time of occurrence of the first peak plasma level after administration with food (6.4 h) was later than, and significantly different from ($P < 0.05$), that after administration after a 12 h fast (4.2 h), but corresponding times of occurrence of the second peak levels were not statistically significantly different. The time required to reach a plasma concentration of 1 $\mu$g/ml after administration with food (5.5 h) was longer than, and significantly different from ($P < 0.05$), that after administration after fasting (3.0 h), as seen from Table V.

Discussion:

Administration of Coating B capsules with food did not affect the extent of drug bioavailability, but the presence of food decreased the rate of bioavailability as indicated by the later, and statistically significantly different, time of occurrence of the first peak plasma level and the time to achieve a plasma concentration of 1 $\mu$g/ml. The phenomenon of the double peak level was also exaggerated after administration with food. Apparently, the extent to which a concomitant meal influences the bioavailability of indomethacin from Coating B capsules is equal to that from a plain indomethacin capsule. It should be emphasized that the observed standard deviations of the bioavailability parameters were of the same order of magnitude when the drug was administered with food or after a fast, as seen from Table V. Thus, the controlled release multiple-units formulation according to the invention represents a reliable and reproducible source of indomethacin when administered with food.

Example 6

Preparation of Furosemide-Containing Cores to be Coated with an Enteric Coating

Cores were prepared from 40 g furosemide, 10 g saccharose powder, 10 g microcrystalline cellulose, 25 g saccharose powder and 15 g talc. The furosemide and 10 g of the saccharose were passed through a grinder using a 0.5 mm sieve.

The powder was mixed with the microcrystalline cellulose, the rest of the saccharose and the talc in a planet mixer.

100 g of the resulting mixture was moistened with 12 g purified water and was mixed until the mixture was a little lumpy.

The moist mixture was extruded through a 0.5 mm sieve.

The resulting extrudate was formed into compact-shaped cores in a marumerizer, and the cores were dried in a fluidized bed; the dried cores were sieved, the upper sieve being 0.71 mm, and the bottom sieve 0.46 mm.

Coating of Cores with Enteric Coating

An enteric coating suspension (C) was prepared by homogenizing 11.4 g Eudragit ® L 30 D together with 0.6 g triacetin and 8 g purified water.

Another enteric coating suspension (D) was prepared by homogenizing 25.0 g Eudragit ® S 12.5 together with 0.375 g acetyltributylcitrate, 2.5 g talc and 22.1 g isopropanol.

Portions of each 100 g of the cores obtained above were coated with coating suspension C and D, respectively, in a fluidized bed, and the resulting pellets were covered with talcum.

The release of furosemide from the resulting pellets was determined as described under MATERIALS AND METHODS. The results are stated in Table VI.

TABLE VI

| Percentage of furosemide released at pH 4.5 and at pH 7.5 (n = 2) | | |
|---|---|---|
| | pH 4.5 | pH 7.5 |
| | 120 m | 30 m |
| Coating C | 16.9 | 95.4 |
| Coating D | 14.3 | 96.5 |

It appears from Table VI than the release of furosemide is practically quantitative at pH 7.5, and that the furosemide is released very slowly at pH 4.5.

Example 7

Preparation of Enteric Coated Acetylsalicylic Acid Crystals

An enteric coating suspension was prepared by homogenizing 59.4 g Eudragit ® S 12.5 together with 0.9 g acetyltributylcitrate, 11.7 g talc and 46.8 isopropanol.

100 g of acetylsalicylic acid crystals having a size from 0.3 to 0.7 mm were coated with 20% (% dry matter of coating, calculated on crystals) of this enteric coating suspension in a fluidized bed.

The dissolution of acetylsalicylic acid from these coated crystals was determined as described under MATERIALS AND METHODS. The results are stated in Table VII.

TABLE VII

| Percentage of acetylsalicylic acid released at pH 1.2, pH 6.5 and pH 7.5 (n = 3) | | |
|---|---|---|
| pH = 1.2 | pH = 6.5 | pH = 7.5 |
| 60 m | 60 m | 60 m |
| 3.2 | 5.7 | 100.0 |

It appears from Table VII that the release of acetylsalicylic acid is practically quantitative at pH 7.5, and that there is only a very slow release at pH 1.2.

For the preparation of a pharmaceutical dosage form, 500 g of the coated crystals obtained above were filled into a capsule No. 00.

LITERATURE

GB Pat. No. 1,468,172

Eur. Patent Application 79 850 110, Publication 0 013 262

U.S. Pat. No. 4 193 985

Baggensen S, Bechgaard H, & Schmidt K (1981) Content and dissolution uniformity testing of controlled-release products: The Repro-Dose ® quality control procedure. *Pharm. Acta Helv* 56, 85–92

Bechgaard, H & Hegermann Nielson, G (1978) Controlled release multiple-units and single-units doses. A literature review. *Drug Develop Ind Pharm* 4, 53–67.

Bechgaard, H & Ladefoged, K (1978) Distribution of pellets in the gastrointestinal tract. The influence on transit time exerted by the density or diameter of pellets. *J. Pharm Pharmacol* 30, 690–692.

Bechgaard, H & Baggesen, S (1980) Propoxyphene and norpropoxyphene: Influence of type of controlled release formulation on intra and intersubject variations. *J. Pharm Sci* 69, 1327–1330.

Bogentoft, C, Carlsson, I, Ekenved, G & Magnusson, A (1978) influence of food on the absorption of acetylsalicylic acid from enteric-coated dosage forms. *Eur J Clin Pharmacol* 14, 351–355.

Green, DM (1966) Tablets of coated aspirin microspherules-A new dosage form. *J. New Drugs* 6, 294–303.

McDonald, P. J., Mather, L. E. & Story, M. J. (1977) Studies on absorption of a newly developed enteric-coated erythromycin base. *J. Clin Pharmacol* 17, 601–606.

Snedecor, G. W. & Cochran, W. G. (1967) Statistical Methods, Iowa State University Press, Iowa, 271–275.

I claim:

1. A pharmaceutical oral controlled release multiple-units formulation, comprising a multiplicity of individual units;

(a) each unit comprising a cross-sectionally substantially homogeneous core coated, in an amount of from 2–25% of the total weight of the core, with an enteric coating which is substantially insoluble at a pH below 7 but soluble in the small intestine, the enteric coating comprising a material selected from the group consisting of acrylic polymers, shellac, cellulose acetate esters, polyvinyl acetate esters, hydroxypropylmethyl cellulose esters, alkyleneglycolether esters, N-butylacrylate-maleic anhydride copolymers, isobutylacrylate-maleic anhydride copolymers and ethylacrylate-maleic anhydride copolymers; and (b) each core being constituted of a multiplicity of particles having average sizes of about 1–10 μm, each of which particles contains:

(i) a sparingly soluble active substance selected from the group consisting of indomethacin, spironolactone, ibuprofen, furosemide, sulfadiazine, sulfamerazine, progesterone, reserpine, pyrvinium embonate, mofebutazone, hydrochlorothiazide, tetracycline, tolbutamide, acetaminophen, testosterone, valporic acid, estradiol, acetazolamide, erythromycin, iron salts, hydralazine, carbamazepine, quinidine, and cardiac glycosides, in an amount of from 10–90% by weight of the particle; and (ii) a readily soluble, dispersion-enhancing substance, in an amount of up to 10% by weight of the active substance, for increasing exposure of the active substance to intestinal fluids, the dispersion-enhancing substance being an anionic surfactant selected from the group consisting of sodium salts of fatty alcohol sulfates, sulfosuccinates, partial fatty acid esters of sorbitans, and partial fatty acid esters of polyhydroxyethylene sorbitans and polyhydroxyethylene fatty alcohol ethers;

the active substance and the dispersion-enhancing substance being co-comminuted with one another to form said particles, and the particles being admixed with a disintegration-enhancing substance comprising (1) a material which is readily soluble in intestinal fluids and is selected from the group consisting of saccharose, glucose, mannitol, sorbitol and lactose, (2) an insoluble material selected from the group consisting of talc, aluminum silicate, zinc oxide, titanium dioxide, colloidal silica and magnesium trisilicate, and (3) mixtures thereof, in an amount of at least 20% by weight of the particles.

2. The formulation of claim 1, in which the enteric coating comprises an acrylic polymer.

3. The formulation of claim 2, in which the enteric coating comprises a copolymer of methacrylic acid and a methacrylic acid methyl ester.

4. The formation of claim 1, in which the active substance is indomethacin.

5. The formulation of claim 1, in which the dispersion enhancing substance is sodium lauryl sulfate.

6. The formulation of claim 1, in which the disintegration-enhancing substance is an insoluble material selected from the group consisting of talc, aluminum silicate, zinc oxide, titanium dioxide, colloidal silica and magnesium trisilicate.

7. The formulation of claim 1, in which the disintegration enhancing-substance comprises a material which is readily soluble in intestinal fluids and is selected from the group consisting of saccharose, glucose, mannitol, sorbitol and lactose.

8. The formulation of claim 1, in which the disintegration-enhancing substance is a mixture of talc and saccharose.

9. The formulation of claim 1, in the form of a capsule containing the multiplicity of individual units.

10. The formulation of claim 9, in which the enteric coating comprises an acrylic polymer.

11. The formulation of claim 10, in which the enteric coating comprises a copolymer of methacrylic acid and a methacrylic acid methyl ester.

12. The formulation of claim 9, in which the active substance is indomethacin.

13. The formulation of claim 1, wherein the active substance is indomethacin, the dispersion-enhancing substance is sodium lauryl sulfate, the disintegration-enhancing substance is a mixture of talc and saccharose, and the enteric coating is a copolymer of methacrylic acid and methacrylic acid methyl ester.

14. The formulation of claim 9, in which the dispersion-enhancing substance is sodium lauryl sulfate.

15. The formulation of claim 9, wherein the active substance is indomethacin, the dispersion-enhancing substance is sodium lauryl sulfate, the disintegration-enhancing substance is a mixture of talc and saccharose, and the enteric coating is a copolymer of methacrylic acid and methacrylic acid methyl ester.

16. The formulation of claim 9, in which the disintegration-enhancing substance is an insoluble material selected from the group consisting of talc, aluminum silicate, zinc oxide, titanium dioxide, colloidal silica and magnesium trisilicate.

17. The formulation of claim 9, in which the disintegration enhancing-substance comprises a material which is readily soluble in intestinal fluids and is selected from the group consisting of saccharose, glucose, mannitol, sorbitol and lactose.

18. The formulation of claim 9, in which the disintegration-enhancing substance is a mixture of talc and saccharose.

* * * * *

UNITED STATES PATENT AND TRADEMARK OFFICE
CERTIFICATE OF CORRECTION

PATENT NO. : 4,606,909

DATED : Aug. 19, 1986

INVENTOR(S) : Helle Bechgaard and Peter Houmøller

It is certified that error appears in the above-identified patent and that said Letters Patent is hereby corrected as shown below:

Cover page, first column, last line: "204156v" should read --204156c--
Cover page, second column, line 5: "Kach" should read --Kala--
Column 7, line 46: before "30 D" insert --L--
Column 11, line 30: "cocomminution" should read --co-comminution--
Column 12, line 10: "Cores containing" should start a new paragraph
Column 13, line 22: "(particular" should read --(particle--
Column 14, line 39: "The present" should start a new paragraph
Column 15, line 2: "ranges" should read --range--
Column 15, line 41: "Indomethacin is" should start a new paragraph
Column 17, line 18: after "46.8" insert --g--
Column 17, line 51: "Nielson" should read --Nielsen--
Column 17, line 63: "influence" should read --Influence--

Signed and Sealed this

Seventeenth Day of March, 1987

*Attest:*

DONALD J. QUIGG

*Attesting Officer*  *Commissioner of Patents and Trademarks*